US006554203B2

United States Patent
Hess et al.

(10) Patent No.: US 6,554,203 B2
(45) Date of Patent: Apr. 29, 2003

(54) SMART MINIATURE FRAGRANCE DISPENSING DEVICE FOR MULTIPLE AMBIENT SCENTING APPLICATIONS AND ENVIRONMENTS

(75) Inventors: Joseph Hess, Bevaix (CH); Joachim Körner, Uhldingen (DE)

(73) Assignee: Ing. Erich Pfeiffer GmbH (DE)

( * ) Notice: Subject to any disclaimer, the term of this patent is extended or adjusted under 35 U.S.C. 154(b) by 0 days.

(21) Appl. No.: 09/942,118

(22) Filed: Aug. 30, 2001

(65) Prior Publication Data

US 2002/0043568 A1 Apr. 18, 2002

(51) Int. Cl.$^7$ ............................................. A01G 27/00
(52) U.S. Cl. ........................... 239/69; 239/70; 239/67; 239/99; 239/102.2
(58) Field of Search ..................... 239/69, 67–68, 239/70, 102.1–102.2, 99, 101, 274, 337, 373, 350, 71; 222/645, 646, 36; 340/603

(56) References Cited

U.S. PATENT DOCUMENTS

| 5,449,117 A | * | 9/1995 | Muderlak et al. ............... 239/6 |
| 5,772,074 A | * | 6/1998 | Dial et al. ....................... 222/1 |
| 5,908,140 A | * | 6/1999 | Muderlak et al. ............... 222/1 |
| 5,924,597 A | * | 7/1999 | Lynn ............................... 222/1 |
| 5,958,346 A | * | 9/1999 | Evans, Jr. ....................... 422/120 |
| 6,036,108 A | * | 3/2000 | Chen .............................. 239/274 |
| 6,039,212 A | * | 3/2000 | Singh ............................. 222/30 |
| 6,062,430 A | | 5/2000 | Fuchs |
| 6,182,904 B1 | * | 2/2001 | Ulczynski et al. .............. 239/1 |
| 6,267,297 B1 | * | 7/2001 | Contadini et al. .............. 239/1 |

FOREIGN PATENT DOCUMENTS

| EP | 0 714 709 A1 | 6/1996 |
| EP | 0 923 957 A1 | 6/1999 |

\* cited by examiner

*Primary Examiner*—Michael Mar
*Assistant Examiner*—Darren W Gorman
(74) *Attorney, Agent, or Firm*—Griffin & Szipl, P.C.

(57) ABSTRACT

The smart fragrance dispensing device (1) has an airless fragrance reservoir (1a) containing a principal medium (8), a flow channel (3) for receiving the principal medium (8), a liquid spray dispenser (2) connected to the reservoir (1a) for dispensing the principal medium (8) as a spray into the flow channel (3), a programmable driving circuit (5) for operating the liquid spray device so as to create the spray consisting of monodispersive droplets, a memory device (4) carrying and communicating identification information about at least the principal medium (8), its dispensing and diffusing characteristics, the liquid spray dispenser (2) and the reservoir (1a), and a programmable control and communication micro-controller unit (7) linked to the reservoir (1a), the information being used to adapt to the individual perception of a user by adjusting to a desired level and memorizing the level.

16 Claims, 3 Drawing Sheets

SMART MINIATURE FRAGRANCE DISPENSING DEVICE FOR MULTIPLE AMBIENT SCENTING APPLICATIONS AND ENVIRONMENTS

FIELD OF THE INVENTION

The present invention concerns a smart fragrance-dispensing device having an electronic control module for allowing dispensing of a specific fragrance as a spray in reply to an electronic command.

BACKGROUND OF THE INVENTION

The document EP-A-0 714 709 already describes a smart fragrance dispenser. This device is arranged for the simultaneous spraying of several stored scents.

The spraying device has two or more cartridges of different capacities, which are fitted to the spray device. The spray device projects their contents from heads supported on a rigid cylindrical tube containing electric wires from a battery and an annular power electronic circuit concentric with the longitudinal axis. Drops of controlled size from one or both cartridges are projected on demand from several ducts under programmed control which is activated e.g. by a proximity detector. Waste is prevented by a safety system switching the device between a standby state and a state of readiness.

However, with such a device, although the amount of ejected fragrance may be controlled, this amount merely depends on the amount programmed to be expelled. If such a device is used to control, e.g. ambient air in a specific surrounding, such as a room or a theatre, there is no way of telling if such amount will suffice or not to control the ambient air. Furthermore, if several different fragrances are to be expelled sequentially from the device, there is a large risk of contamination of a second fragrance by a first as no means are provided for ensuring a full evacuation of the first fragrance without any residue being left in the spray means.

The present invention has as its aim to overcome the above-mentioned problems. Furthermore, the present invention aims to provide a smart fragrance dispensing device capable of precisely controlling the expelled fragrance in view of its user's requirements and/or in view of the location in which the device is being used.

SUMMARY OF THE INVENTION

Thus, the present invention concerns a smart fragrance-dispensing device as defined in the appended claims.

Thanks to the smart fragrance-dispensing device of the present invention, it is possible to adapt the expelled fragrance to the individual perception of the user by means of adjusting to a desired level and memorising this level.

Furthermore, the present invention also allows controlling the ambient atmosphere of the environment in which the user of the device is present.

BRIEF DESCRIPTION OF THE DRAWINGS

Other features and advantages of the smart fragrance-dispensing device according to the present invention will become clear from reading the following description, which is given solely by way of a non-limitative example thereby referring to the attached drawings in which:

FIG. 1A is a schematic view of a preferred embodiment of the smart fragrance-dispensing device according to the present invention, FIG. 1B shows an exploded view of the device of FIG. 1a.

DETAILED DESCRIPTION OF THE PREFERRED EMBODIMENTS

Figures 1A, 1B:
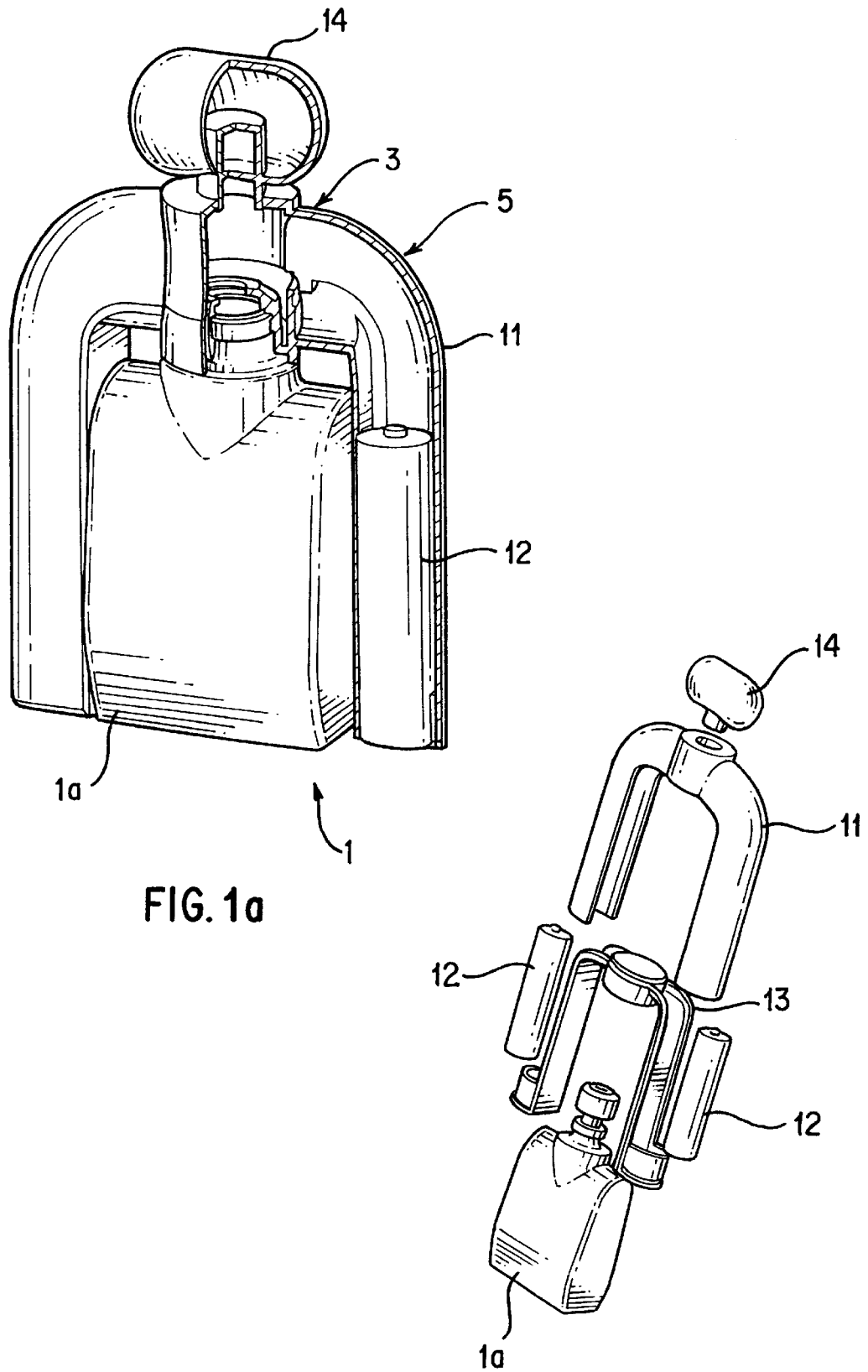

As shown in FIG. 1, the smart fragrance-dispensing device 1 according to the present invention may be formed in a compact manner. The device shown is a handheld battery-operated device. Smart miniature fragrance dispensing device 1 consists of an exterior housing 11 for accommodating the different components constituting the device. A frame 13 is further provided which may contain a power source, such as two batteries 12 for powering the device. Of course, the power supply may be any other suitable low-power source, such as a car power supply, solar supply or the like. Housing 11 comprises a containment space for at least one airless fragrance reservoir 1a. Preferably, this reservoir 1a has an active or passive delivery system and contains a principle fragrance medium, referenced 8 (see FIG. 2). Advantageously, built into or otherwise arranged within the containment space of reservoir 1a, a compensating reservoir, not shown, may be provided for containing a compensation medium which gradually fills the part of which has become free of reservoir 1a due to expelling of principle medium 8. Such a reservoir and its complementary compensating reservoir are already known as such, and are described, e.g., in the document U.S. Pat. No. 6,062,430, which is incorporated herewith by reference. In short, the reservoir, in fact, contains a first and a second volume respectively filled with a first medium, in the present case the principle medium, and a second medium, wherein the first and second volumes are operationally variable. Preferably, this reservoir is encapsulated to avoid contamination, evaporation, atmospheric influences (UV etc.) of the principle medium and allows to operate the device without adding any preservatives, stabilisers etc. to the principle medium, as also explained in the above-mentioned U.S. Pat. No. 6,062,430. Of course, other airless reservoirs such as capillary tubes or aluminium bags may be used.

Reservoir 1a is provided with a liquid spray dispenser 2 (see FIG. 2) for dispensing principle medium 8 into a flow channel 3 which is arranged, for instance, within the top part of housing 11 to receive the principle medium as a spray of droplets. Preferably, flow channel 3 is a controllable induced mixed media flow channel for mixing principle medium 8 dispensed from reservoir 1a with an ambient medium 8b, such as a gas, contained within the flow channel, as will be explained in more detail further on. The flow channel expels the mixed media through an outlet provided in housing 11 so as to allow the fragrance to enter the environment.

Housing 11 further contains electronic circuitry suitably arranged for driving liquid spray dispenser 2 and for controlling flow channel 3, and activation means 14 for activating the electronic circuitry and for expelling the fragrance. Such activation means may be for example a simple push button provided on the top of housing 11.

Preferably, airless fragrance reservoir 1a is assembled in a leak-tight manner to spray dispenser 2.

Figure 2:
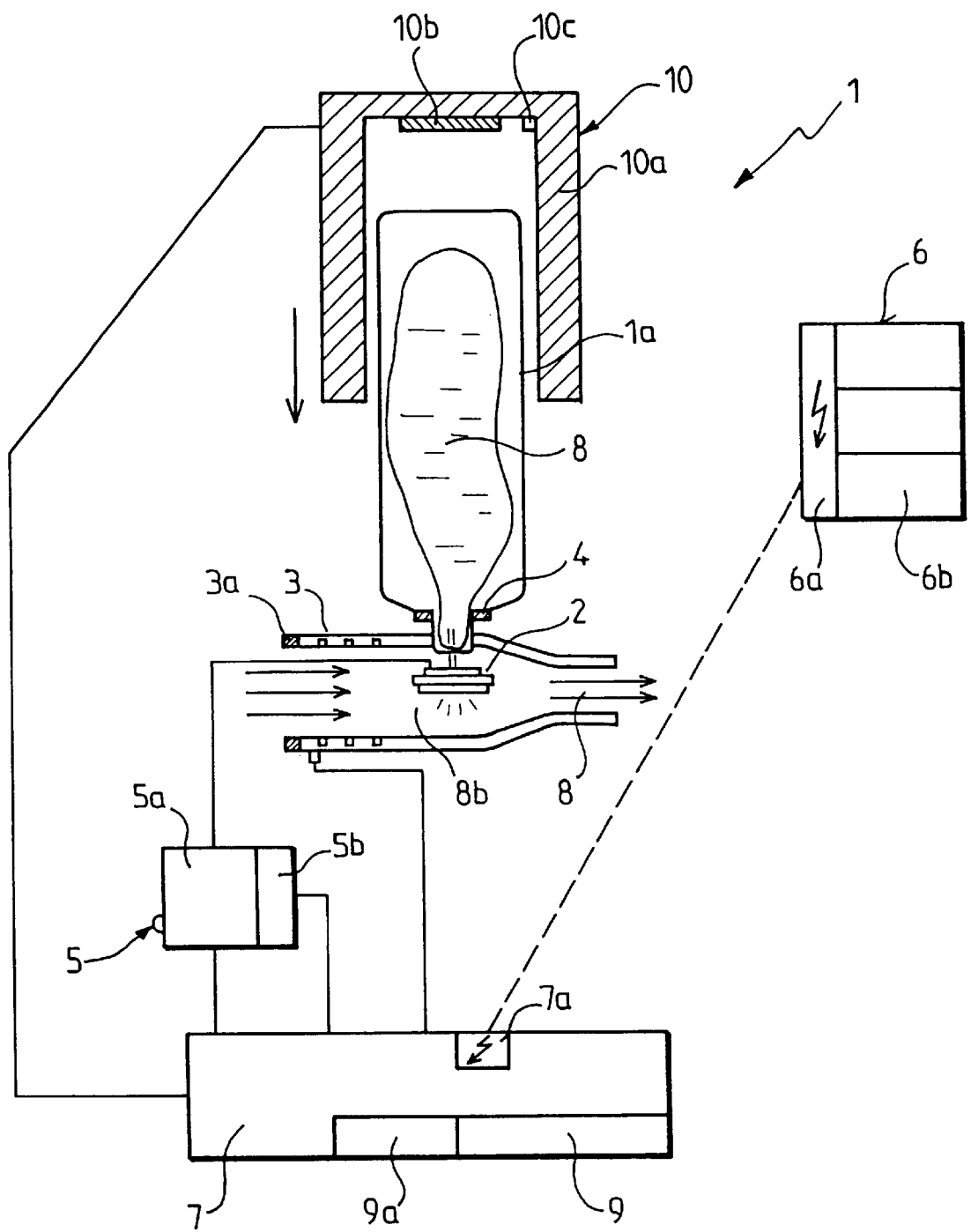
FIG. 2 shows a detailed view of the device of FIG. 1.

Reference will now further be made to FIG. 2. The above-mentioned electronic circuitry contained within smart fragrance dispensing device 1 further comprises at least one memory or other electronic device 4 carrying and communicating identification information about at least principle medium 8 itself, for instance a fragrance, its dispensing and diffusing characteristics, and about the smart fragrance dispensing device 1 and/or its reservoir 1a.

Flow channel 3 may consist of a plastic part as represented in FIG. 2 in which heaters may be provided in the form of flow inducing elements 3a providing controlled flows of the sprayed principle medium 8 for dispersion into the induced flow of the ambient medium as largely monodispersive droplets of a range of approximately from about 1 to 10 μm, but preferably smaller than 10 μm in diameter. Flow inducing elements 3a may be in the form of tungsten rings which are individually and sequentially electrically connected in order to create a controlled "chimney effect", i.e. a directed flow of the ambient medium 8b through the flow channel before, during and after the principle medium 8 is dispersed therein, for carrying the mixed media outwards in an efficient manner. In fact, it is possible to regulate the activation of the Tungsten rings by applying different currents to the rings so as to control the intensity of the rings thus creating a temperature gradient due to the fact that different rings will heat more or less quickly. Further, the time of applying the current may also be varied. The controlled combination of temperature gradient and actuation time regulates the passage of the principle medium into the gaseous phase and with that the controlled dispersion of the fragrance as a function of its properties, such as its volatility, its dispersion ratio, its intensity and the like, into the surrounding environment or room. Thus, this controlled "chimney effect" allows for a control of the absence or presence of the fragrance.

Of course, instead of heating elements, a fan could be used to create such a "chimney effect", although a fanless, thermal convection solution is preferred.

Preferably, heating elements 3a also stay on for a given time after the dispensing in order to ensure that the flow carries out all the remnants of the sprayed fragrance. This is especially important when several fragrances are expelled sequentially so as to avoid mutual contamination.

Liquid spray dispenser 2 is arranged for expelling the principle medium 8 through a non-vibrating membrane substrate having non-vibrating, straight output channels, and which extracts the principle medium directly in a valve-less configuration from airless fragrance reservoir 1a. Preferably, dispenser 2 is constituted by a liquid droplet spray device according to European patent application publication number EP-A-0 923957. Thus, spray dispenser 2 comprises a housing formed by a top-substrate and a bottom-substrate with a space there between for receiving principle medium 8. Ultrasonic vibrating means are arranged on the bottom substrate for vibrating such and for thus forcing the liquid medium through straight outlet channels and nozzles provided in the non-vibrating top substrate so as to expel a spray of monodispersive droplets, as explained in detail in the above-mentioned European application. Dispenser 2 may further be provided with a protection against fragrance evaporation, and is positioned top or bottom up or in any suitable position in space in conjunction with the controllable induced mixed media flow channel 3.

The electronic circuitry within the inventive dispensing device 1 further comprises at least one programmable, miniaturised very low energy ultrasonic driver circuit 5 for driving in a valve-less configuration the smart fragrance dispensing device 1 in conjunction with the ultrasonic spray dispenser 2 and providing sensor-less information on the full/empty state of fragrance dispensing device 1.

Figure 3:
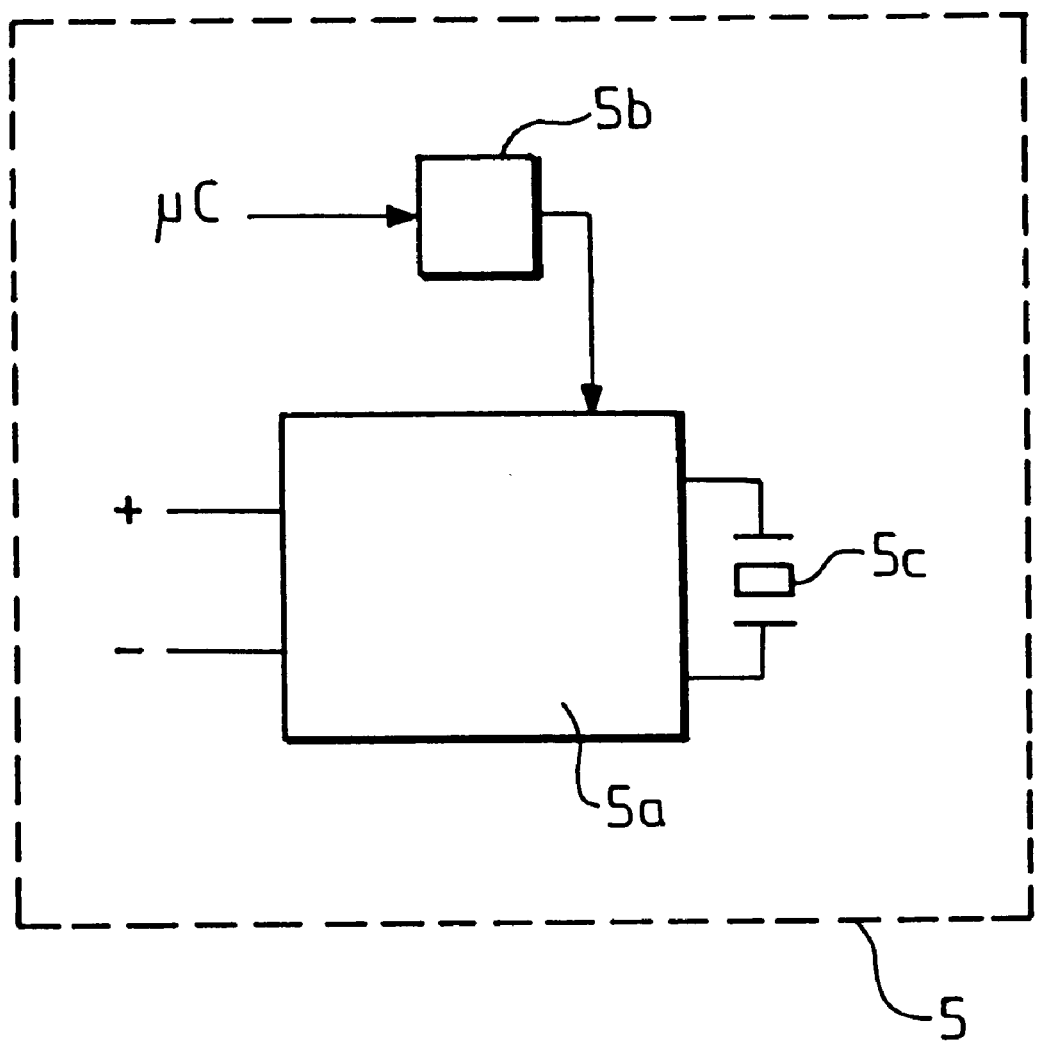
FIG. 3 shows a schematic diagram of a driver circuit for driving the present smart fragrance-dispensing device.

FIG. 3 shows in more detail the diagram of ultrasonic driver circuit 5. Driver circuit 5 comprises a piezoelectric driving circuit 5a containing a transistor, not shown, for exciting piezoelectric element 5c, which thus constitutes the ultrasonic vibrating means of liquid spray dispenser 2, so as to cause the latter to vibrate. Such driving circuits are well known as such and will thus not be described in detail here. A driver programmable switch 5b is further provided to allow control of the driving circuit 5a. Switch 5b is connected to a micro-controller forming part of the electronic circuitry, as will be explained in detail further on.

Referring back to FIG. 2, preferably, at least one multi-sensor unit 6 is further provided. Each unit may be a separated module that can be operatively linked to smart fragrance-dispensing device 1, and is preferably temperature compensated and may be battery or mains powered. Multi-sensor unit 6 consists of at least one ambient air flow sensor and at least one calibrated ambient medium characteristics sensor or sensor-array, for sensing the ambient air motion and condition as compared to a pre-calibrated reference level and the absence or presence and the increase or decrease of the concentration of the principle medium in the ambient medium, e.g. the air of a room. Thus, by detecting a variation in the air condition or motion, it is thus possible to release the fragrance in a controlled manner.

A non-disposable control and communication microcontroller unit 7 is further provided for controlling the smart fragrance dispensing device 1, the multi-sensor unit 6, the ultrasonic driver circuit 5, as mentioned above this driver is micro-controlled, and the mixed media flow channel 3. Control and communication unit 7 may be of the wired or wireless type and it controls ultrasonic driver circuit 5 and mixed media flow channel 3 in such a manner that the induced mixed media flow is started in time before the driver circuit is activated and stopped in time after the driver circuit is deactivated and otherwise in function of information read from memory device 4, this information being used to adapt to the individual perception of a user by means of adjusting to a desired level and memorising said level.

As can be seen in FIG. 2, control and communication unit 7 and multi-sensor unit 6 are linked in a wireless manner. To this effect, control and communication unit 7 and multi-sensor unit 6 are each provided with a wireless transceiver, respectively referenced 7a and 6a allowing for the wireless communication.

Control and communication unit 7 controls and commands the dispensing from smart fragrance dispensing unit 1 via the programmable, ultrasonic driver circuit(s) 5 and mixed media flow channel 3 in accordance with rule-based instructions and information derived from the dispensing characteristics contained in and read from memory device 4 and further in accordance with information read from multi-sensor unit 6 and calculations performed based on the desired presence or absence of single or multiple principle media or components in the ambient medium, (the calculations being performed as simple rule, fuzzy logic rule, neural network or virtual sensor quantification rule processing).

The desired concentration level(s) of single or multiple principle media in the ambient medium, their sequence of dispensing, their time of presence or absence in the ambient medium and their rate of diffusion, their availability, their concentration as read by multi-sensor unit 6 are adjustable either directly in control and communication unit 7 or remotely via an interface 9 built-in control and communication unit 7. This remote control may be carried out, e.g. by telephone, PC, Net appliance etc or Internet communication line or wireless communication, Bluetooth™, and the like, and according to the applicable communication protocols for such devices, web-appliances etc. However, this interface may of course also be voice-controlled.

Interface 9 is provided with communication means 9a which are suitably arranged on the software and/or hardware level to communicate with audio/video synchronising, sequencing, time lead or lag with regards to video or audio and depending on the properties of the fragrance, e.g. its volatility or dispersion ratio etc., thereby controlling instructions for example on movie projectors. For example, in the MPEG standard, subtitles are triggered using a signal just before the frame requiring the subtitle appears. This trigger signal, or a similar signal, may be used for audio synchronising and for the control of the time lag or time lead. The time lag/lead may be varied as a function of the properties of the fragrance. Indeed, as may be understood, if a fragrance dispenses quickly into the surrounding air, the release command may be triggered later than if the dispensing ratio is slow.

In analogy, communication unit 7 is compatible with the applicable multi-media, hypermedia and AV protocols such that interface 9 may be used for the dispensing of single or multiple fragrances, of their time of presence or absence in the ambient air, information about their availability, their rate of diffusion and their concentration as read by the non-disposable multi-sensor unit(s), all of which can be controlled, synchronised by or sequenced with information contained in the respective multimedia support and storage system.

Thus, the innovation of the present smart fragrance dispensing unit lies principally in the use in multimedia application which results from the miniature and smart concept which allows interfacing with the various multimedia standards mentioned and incorporation into a variety of media from cinema seats to PlayStatations™, PC's, Net-appliances or point-of-sale terminals. Thus, the fragrance dispenser with the multi-sensor unit constitutes a "system" that allows this flexibility, exchangeability of cartridges and adaptability to environments and liquids to be dispensed.

In a further embodiment, control and communication unit 7 is suitably equipped and compatible with the applicable multimedia, hypermedia, Digital Video Broadcasting (DVB) as well as interactive AV protocols, codes and interpreters according to the relevant JPEG, MPEG and MHEG standards, as expressed in the corresponding ISO/IEC documents or according to other proprietary standards or methods in video processing like USB protocol layers (e.g. chapter 8) or QuickTime™ encoding and audio processing (e.g. MIDI, or Dolby™ digital, LPCM, MP3, AAC (Advanced Audio Coding) etc) or as used in video games and other proprietary audio, video, AV and computer graphics techniques and devices.

This interface 9 is being used for orchestrating the dispensing of single or multiple fragrances, of their time of presence or absence in the ambient air, information about their availability, their rate of diffusion and their concentration as read by the multi-sensor unit(s) 6, all of which can be controlled, synchronised by or sequenced with moving picture, animation, video or audio content, objects etc as contained in the respective multimedia support and storage systems like DVD's and others and related devices, including broadcasting, set-top-boxes, interactive retrieval, VoD (Video on Demand) etc and as can be used in various public or private electronic media environments. Thus, it is further possible to trigger the dispensing of scents to accompany an AV message content.

In fact, such use of scents may be applied to certain private and public multimedia applications, such as cinemas, home multimedia centres, multimedia viewing and interactive installations and centres, home-shopping, interactive advertising, advertising on point-of-sale or information etc, where the scents are used to accentuate, expand or complement or other accompany the AV message content. The multi-sensor unit(s) are then located directly in or in close vicinity of the enclosure housing 11 of liquid spray dispenser 2, the ultrasonic driver circuit 5 and the control and communication unit 7 and is connected in a wired or wireless way and where the control and communication unit (7) can be addressed remotely via telephone, or Internet or wireless communication, Bluetooth™ or other.

Multi-sensor unit 6 may further comprise a presence sensor, referenced 6b, for applications in public environments, e.g. in cinemas, buses, aeroplanes, public washrooms etc, where the smart fragrance dispensing device is arranged in close vicinity of a consumer, e.g. by building it into the back of the seat or the front panel, to detect the presence of the consumer so as to initiate or block the functioning of the smart fragrance dispensing device.

Housing 11 of smart fragrance dispensing device 1 preferably consists of at least one non-disposable cartridge 10 into which reservoir 1a is fitted. This cartridge may be provided with suitable thermal insulation 10a, an electronically controlled Pelletier element or elements 10b and a temperature sensor 10c, which are controlled by the control and communication unit 7 to maintain reservoir 1a at ambient temperature to avoid evaporation of its content.

In an advantageous arrangement, control and communication unit 7 is arranged to control the air-conditioning system of an environment in which said housing is arranged before or as a user enters it.

Multi-sensor unit 6 may be used to detect a certain concentration of a certain, first medium, e.g. cigarette smoke, in the second, ambient medium of the environment in which the device is placed and to release a third medium, e.g. a fragrance, to cover the effect of the first medium by releasing a calculated amount of the third medium.

Advantageously, for certain private and public places of usage for the present smart fragrance dispensing device, the reservoir 1a is constituted by a different airless system, for example a multilayer polymer/aluminium/polymer bag containing the principle medium 8 and into which at least one spray dispensing device 2 is assembled leak-tight and connected to the other units.

The principle media contained within reservoir 1a may be a fragrance, insect repellent, air disinfectant, air humidification, (aromatic) essence, food or other flavour replicating liquids and volatiles to be dispensed in order to obtain the desired characteristic of the ambient medium of the room or environment in which the present inventive device is placed for operation.

In a further advantageous embodiment, smart fragrance dispensing device 1 serves to dispense a paramedical substance and comprises a specific sensor for adjustment of the dispensed volume, timing incl. biorhythm and circadian rhythm and concentration of such substance.

As may be understood from the above, the present invention allows for a miniaturised, very simple, very cost effective device can grow into a smart system by modular expansion of its units. Further, thanks to the cost-effective multi-sensor, ambient characteristics may be detected for user perception controlled dispensing.

Advantageously, liquid spray dispenser 2 may be operated in such a way that by using a wrong frequency, i.e. not the exact resonance frequency of the piezoelectric vibration means, the dispenser will heat up during a short period of time in order to evacuate the fragrance from the internal volume. The internal volume of the liquid spray dispenser 2 needs to be minimal, preferably from less than 1 µl to several µl.

Preferably, multi-sensor unit 6 is composed of at least one ambient air flow sensor and at least one calibrated ambient medium characteristics sensor or sensor array, and uses information from the airflow (direction, flow rate, vectors) which can be combined with information from the sensor array and the memory device 4 related to the characteristics of the principle medium 8 to conclude on the emission of the principle medium fragrance needed to maintain a desired level of fragrance in a given environment, the air renewal rate, the volitilisation of the principle medium etc.

As such, it is possible for the user to adapt the dispensed fragrance to the individual perception of the user by means of adjusting to a desired level and memorising said level.

The sensor array can be of the metal oxide, semiconductor (solid state), conducting polymer or electronic nose type. Important is the notion of <<calibrated ambient medium characteristics sensor ambient medium being "synthetic air" versus any ambient air detected at a given moment anywhere and the ambient air resulting from the emission of the principle medium into that ambient air. Calibrated also means that the electronics which processes the information from the sensor array <<knows >> e.g. has been pre-calibrated to at least one <<signature or the fingerprint >> of a particular principle medium or a variety of such media.

Preferably, the multi-sensor unit should be operated at a temperature that is sufficiently high (usually more than 400 and less than 600° C. for a semiconductor sensor) in order to avoid condensation and influence of humidity in the air. It should also be operated to control drift.

Having described a preferred embodiment of this invention, it will now be apparent to one of skill in the art that other embodiments incorporating its concept may be used. It is felt, therefore, that this invention should not be limited to the disclosed embodiment, but rather should be limited only by the scope of the appended claims.

What is claimed is:

1. Smart fragrance dispensing device having a housing and comprising:
    a power supply;
    an airless fragrance reservoir containing a principal liquid medium;
    a flow channel for receiving said principal liquid medium;
    a liquid spray dispenser connected to said reservoir for dispensing said principal liquid medium as a spray into said flow channel;
    a programmable driver circuit for operating said liquid spray device so as to create said spray consisting of monodispersive droplets;
    a memory device carrying and communicating identification information about at least said principal liquid medium, its dispensing and diffusing characteristics, said liquid spray dispenser and said reservoir; and
    a programmable control and communication micro-controller unit at least linked to said reservoir, said programmable driver circuit, and said flow channel; said control and communication unit being of the wired or wireless type and controlling said programmable driver circuit and said flow channel in such a manner that the flow of said principal liquid medium is started in time before the driver circuit is activated and stopped in time after the driver circuit is activated to provide a predetermined amount of said principal liquid medium delivered to said liquid dispenser as a function of information read from said memory device, said information being used to adapt to the individual perception of a user by means of adjusting said predetermined amount of said principal liquid medium to a desired level of said monodispersive droplets and memorizing said level.

2. Smart fragrance dispensing device according to claim 1, wherein said flow channel is a mixed media flow channel having an ambient medium therein, and wherein said programmable control and communication micro-controller unit is further also linked to the mixed media flow channel in such a manner that the mixed media flow is started in time before the driver circuit is activated and is stopped in time after the driver circuit is activated as a function of the information read from said memory device.

3. Smart fragrance dispensing device according to claim 1, further comprising at least one multi-sensor unit provided as a removable module and operatively linked to the smart fragrance dispensing device and consisting of at least one ambient air flow sensor and at least one ambient medium characteristics sensor, said multi-sensor unit sensing the ambient air motion and condition, as compared to a pre-calibrated level, as well as the absence or presence and the variation of the concentration of said principal liquid medium in said ambient medium, wherein said programmable control and communication micro-controller unit is further also linked to the multi-sensor unit.

4. Smart fragrance dispensing device according to claim 3, wherein said control and communication unit further comprises a built-in interface and controls and commands the dispensing from said reservoir via said programmable driver circuit and said controllable mixed media flow channel in accordance with rule-based instructions and information derived from said dispensing characteristics contained in and read from said memory device and further in accordance with information read from said multi-sensor unit(s) and calculations performed based on the desired presence or absence of single or multiple principle media or components in the ambient medium, the desired concentration level(s) of said single or multiple principle media in the ambient medium, their sequence of dispensing, their time of presence or absence in the ambient medium and their rate of diffusion, their availability, their concentration as read by said non-disposable multi-sensor unit(s) being adjustable either directly in the non-disposable control and communication unit or remotely via said built-in interface.

5. Smart fragrance dispensing device according to claim 4, wherein said interface is a voice-controlled interface.

6. Smart fragrance dispensing device according to claim 4, wherein said interface comprises communication means which are suitably arranged on the software and/or hardware level to communicate with multimedia systems such that said interface is used for the dispensing of single or multiple fragrances, of their time of presence or absence in the ambient air, information about their availability, their rate of diffusion and their concentration as read by said multi-sensor unit, all of which being controlled, synchronised by or sequenced with information contained in the respective multimedia system.

7. Smart fragrance dispensing device according to claim 3, wherein said multi-sensor unit further comprises a proximity detector for detecting the presence of a person in the same environment as in which said smart fragrance dispensing device is located so as to control its operation.

8. Smart fragrance dispensing device according to claim 6, wherein said interface receives control commands from said multimedia system for triggering the dispensing of a fragrance as a function of the output of said multimedia system.

9. Smart fragrance dispensing device according to claim 1, wherein said housing comprises a temperature sensor and thermal control means arranged to maintain said reservoir at ambient temperature.

10. Smart fragrance dispensing device according to claim 1, wherein said principal medium is a fragrance, an insect repellent, an air disinfectant, an air humidification, an essence, or a food or other flavour replicating liquids and volatiles.

11. Smart fragrance dispensing device according to claim 2, further comprising at least one multi-sensor unit provided as a removable module and operatively linked to the smart fragrance dispensing device and consisting of at least one ambient air flow sensor and at least one ambient medium characteristics sensor, said multi-sensor unit sensing the ambient air motion and condition, as compared to a pre-calibrated level, as well as the absence or presence and the variation of the concentration of said principal medium in said ambient medium, wherein said programmable control and communication micro-controller unit is further also linked to the multi-sensor unit.

12. Smart fragrance dispensing device according to claim 11, wherein said control and communication unit further comprises a built-in interface and controls and commands the dispensing from said reservoir via said programmable driver circuit and said controllable mixed media flow channel in accordance with rule-based instructions and information derived from said dispensing characteristics contained in and read from said memory device and further in accordance with information read from said multi-sensor unit(s) and calculations performed based on the desired presence or absence of single or multiple principle media or components in the ambient medium, the desired concentration level(s) of said single or multiple principle media in the ambient medium, their sequence of dispensing, their time of presence or absence in the ambient medium and their rate of diffusion, their availability, their concentration as read by said non-disposable multi-sensor unit(s) being adjustable either directly in the non-disposable control and communication unit or remotely via said built-in interface.

13. Smart fragrance dispensing device according to claim 12, wherein said interface is a voice-controlled interface.

14. Smart fragrance dispensing device according to claim 12, wherein said interface comprises communication means which are suitably arranged on the software and/or hardware level to communicate with multimedia systems such that said interface is used for the dispensing of single or multiple fragrances, of their time of presence or absence in the ambient air, information about their availability, their rate of diffusion and their concentration as read by said multi-sensor unit, all of which being controlled, synchronised by or sequenced with information contained in the respective multimedia system.

15. Smart fragrance dispensing device according to claim 11, wherein said multi-sensor unit further comprises a proximity detector for detecting the presence of a person in the same environment as in which said smart fragrance dispensing device is located so as to control its operation.

16. Smart fragrance dispensing device according to claim 14, wherein said interface receives control commands from said multimedia system for triggering the dispensing of a fragrance as a function of the output of said multimedia system.

* * * * *